(12) United States Patent
Nielsen et al.

(10) Patent No.: US 9,212,266 B2
(45) Date of Patent: Dec. 15, 2015

(54) HYDROPHILIC GELS FROM POLYALKYLETHER-BASED PHOTOINITIATORS

(71) Applicant: Coloplast A/S, Humlebaek (DK)

(72) Inventors: Christian B Nielsen, Dragoer (DK); Niels Joergen Madsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/316,821

(22) Filed: Jun. 27, 2014

(65) Prior Publication Data

US 2014/0378572 A1    Dec. 25, 2014

Related U.S. Application Data

(63) Continuation of application No. 13/805,104, filed as application No. PCT/DK2011/050226 on Jun. 22, 2011, now Pat. No. 8,841,354.

(30) Foreign Application Priority Data

Jun. 22, 2010 (DK) .................................. 2010 70282
May 31, 2011 (DK) .................................. 2011 70272

(51) Int. Cl.
*C08F 2/50*       (2006.01)
*C08F 2/46*       (2006.01)
*C08G 61/04*      (2006.01)
*C08J 3/28*       (2006.01)
*A61L 29/08*      (2006.01)
*A61L 29/14*      (2006.01)
*C08G 65/22*      (2006.01)
*C08J 3/075*      (2006.01)
*A61L 29/06*      (2006.01)

(52) U.S. Cl.
CPC .. *C08J 3/28* (2013.01); *A61L 29/06* (2013.01); *A61L 29/085* (2013.01); *A61L 29/14* (2013.01); *A61L 29/145* (2013.01); *C08F 2/50* (2013.01); *C08G 65/22* (2013.01); *C08J 3/075* (2013.01); *A61L 2400/10* (2013.01); *C08J 2300/14* (2013.01); *C08J 2371/02* (2013.01); *C08J 2375/08* (2013.01); *C08L 2312/06* (2013.01)

(58) Field of Classification Search
CPC ...... C08J 3/28; C08J 2300/14; C08J 2371/02; C08J 3/075; C08J 2375/08; C08G 65/02; C08F 2/50; A61L 29/06; A61L 29/145; A61L 29/085; A61L 29/14; A61L 2400/10; C08L 2312/06; C08L 71/02
USPC ............. 522/35, 33, 6, 71, 189, 184, 1; 520/1
See application file for complete search history.

(56) References Cited

U.S. PATENT DOCUMENTS

| 4,785,059 | A  | * | 11/1988 | Fydelor et al. ................ | 525/301 |
| 2006/0004116 | A1 | * | 1/2006 | Kishi et al. ..................... | 522/146 |
| 2010/0049146 | A1 | * | 2/2010 | Nielsen et al. ................ | 604/265 |
| 2013/0089582 | A1 | * | 4/2013 | Nielsen et al. ................ | 424/400 |

FOREIGN PATENT DOCUMENTS

| JP | 2007-045959 | * | 2/2007 |
| JP | 2007045959 A2 |   | 2/2007 |
| WO | 2008-071796 | * | 6/2008 |
| WO | 2011103878  |   | 9/2011 |

OTHER PUBLICATIONS

Suzuki et al, JP 2007-045959 Machine Translation, Feb. 22, 2007.*
Office Action mailed on Feb. 13, 2015 in U.S. Appl. No. 14/316,821.

* cited by examiner

*Primary Examiner* — Ling Choi
*Assistant Examiner* — Jessica E Whiteley
(74) *Attorney, Agent, or Firm* — Coloplast Corp., Coloplast A/S; Nick Baumann

(57) ABSTRACT

The invention provides a method for the manufacture of a catheter comprising a hydrophilic gel. The method comprising the steps of combining a polymeric photoinitiator of the general formula (I):

$$R_1(A_1)_r\text{-}(R_2(A_2)_m\text{-}O)_o\text{---}(R_3(A_3)_n\text{-}O)_p\text{---}R_4(A_4)_s \quad (I)$$

with one or more gel-forming polymers and/or gel-forming monomers to form a matrix composition, curing the matrix composition by exposing it to UV radiation, exposing the matrix composition to a swelling medium and incorporating the hydrophilic gel into a catheter.

22 Claims, 4 Drawing Sheets

HYDROPHILIC GELS FROM POLYALKYLETHER-BASED PHOTOINITIATORS

FIELD OF THE INVENTION

The present invention relates to a method for making a catheter comprising a hydrophilic gel and the catheter thereby obtained. The invention also relates to methods for manufacturing hydrophilic gels using polymeric photoinitiators, and the hydrophilic gels thus obtained. Medical devices comprising said hydrophilic gels are also provided.

BACKGROUND OF THE INVENTION

Curing of coatings through ultraviolet (UV) radiation, thereby resulting in a coating for use as a gel (e.g. a hydrogel), requires efficient methods of initiating the chemical reaction responsible for the curing process. Cross-linking of polymeric material through generation of radical species upon irradiation with UV light is widely used to produce hydrogels for medical device coatings. Coating compositions with polyvinylpyrrolidone and a photoinitiator as the main constituents, which are cured with UV irradiation, are often used for producing hydrogels. The photoinitiators used in these processes can be either oligomeric or polymeric. Oligomeric photoinitiators are partially free to diffuse to the surface of the cured material, thereby rendering these substances exposed to the environment.

WO 2008/012325 and WO 2008/071796 describe photocuring of plastic coatings for medical devices.

Other published documents which relate to polymeric photoinitiators based on polyalkylethers are US 2007/0003588 and Xuesong Jiang et al, Polymer, 50 (2009) 37-41.

OBJECT OF THE INVENTION

It is an object of the invention to provide a method for the manufacture of catheters comprising hydrophilic gels, and the hydrophilic gels themselves. The photoinitiators can be a component of, or constitute the entire hydrophilic gel.

SUMMARY OF THE INVENTION

It has been found by the present inventors that polymeric photoinitiators with certain structures can be used in the formation of hydrophilic gels and medical devices, such as catheters.

The present invention therefore relates to method for manufacturing a catheter comprising a hydrophilic gel, said method comprising the steps of:
a. combining a polymeric photoinitiator of the general formula I:

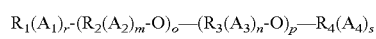

$$R_1(A_1)_r\text{-}(R_2(A_2)_m\text{-}O)_o\text{—}(R_3(A_3)_n\text{-}O)_p\text{—}R_4(A_4)_s \quad (I)$$

with one or more gel-forming polymers and/or gel-forming monomers to form a matrix composition,
b. curing the matrix composition obtained in step a. by exposing it to UV radiation,
c. exposing the matrix composition to a swelling medium,
d. incorporating the hydrophilic gel/matrix composition into a catheter,
wherein steps b. and c. may take place in any order, provided that, if step d. is carried out first, step b. takes place before step c.

In the above polymeric photoinitiator of formula (I), $R_2$ and $R_3$ are independently at each occurrence identical or different, linear or branched alkylene or cycloalkylene groups; wherein $R_2$ and $R_3$ may be substituted with one or more substituents selected from CN; azides, esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group.

$R_1$ and $R_4$ are independently at each occurrence identical or different, linear or branched alkyl or cycloalkyl groups or aryl groups or are independently at each occurrence selected from H, OH, CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, polyethylenes, polyethylene oxides, polyvinyl pyrrolidones, polypropylenes, polyesters, polyamides, polyacrylates, polystyrenes, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group.

o and p are each a real number from 0-5000 provided that o+p>0. m and n are each a real number from 0-10, provided that m+n>0; r and s are each a real number from 0-5; and $A_1$, $A_2$, $A_3$ and $A_4$ are identical or different photoinitiator moieties.

A catheter is also provided which is obtainable via the method above. The invention also provides a catheter, wherein the hydrophilic gel is coated on at least a surface portion thereof.

The polymeric photoinitiators of the invention can also "self-cure" or "auto-cure". The invention therefore provides a method for the manufacture of a hydrophilic gel, said method comprising the steps of:
a. providing a polymeric photoinitiator of the general formula I:

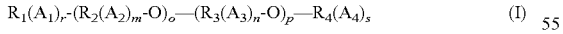

$$R_1(A_1)_r\text{-}(R_2(A_2)_m\text{-}O)_o\text{—}(R_3(A_3)_n\text{-}O)_p\text{—}R_4(A_4)_s \quad I$$

wherein $R_2$ and $R_3$ are independently at each occurrence identical or different, linear or branched alkylene or cycloalkylene groups; wherein $R_2$ and $R_3$ may be substituted with one or more substituents selected from CN; azides, esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;

$R_1$ and $R_4$ are independently at each occurrence identical or different, linear or branched alkyl or cycloalkyl groups or aryl groups or are independently at each occurrence selected from H, OH, CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, polyethylenes, polyethylene oxides, polyvinyl pyrrolidones, polypropylenes, polyesters, polyamides, polyacrylates, polystyrenes, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;

o and p are each a real number from 0-5000 provided that o+p>0;

m and n are each a real number from 0-10, provided that m+n>0;

r and s are each a real number from 0-5; and $A_1, A_2, A_3$ and $A_4$ are identical or different photoinitiator moieties;

b. exposing the polymeric photoinitiator from step a. to UV radiation, and c. exposing the polymeric photoinitiator to a swelling medium, wherein steps b. and c. may take place in any order.

In the case where the swelling medium is water, a hydrogel is obtained.

Further aspects of the invention include a hydrophilic gel obtainable via the "auto-curing" method, a medical device comprising this hydrophilic gel.

LEGENDS TO THE FIGURES

DETAILED DISCLOSURE OF THE INVENTION

Definitions

Figure 1:
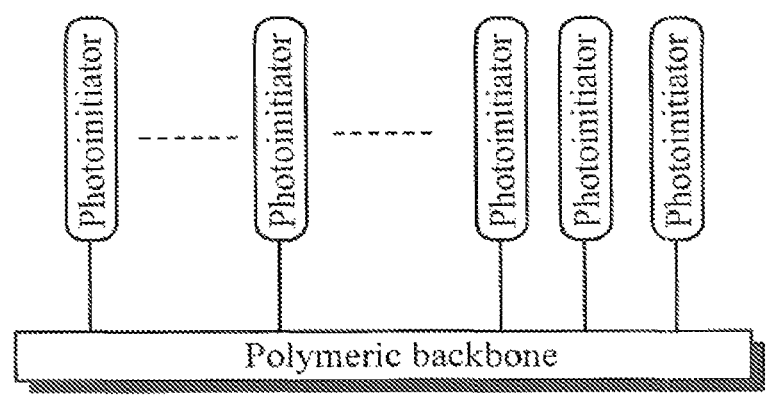
FIG. 1 illustrates a general motif of polymeric photoinitiators, with photoinitiator moieties pendant on a polyalkylether.
Figure 2:
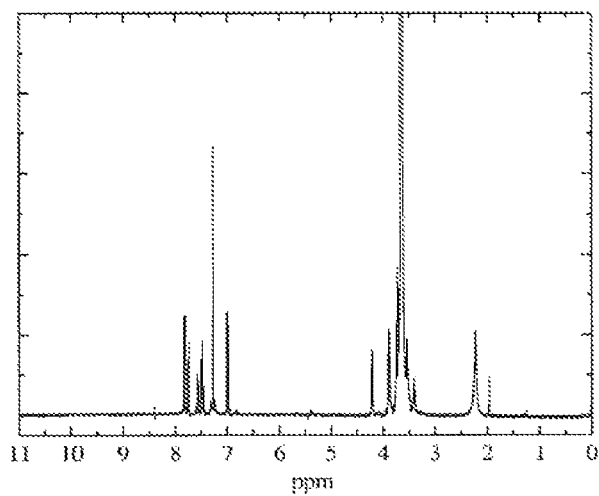
FIG. 2 shows the $^1$H-NMR spectrum of poly-co-ethyleneoxid-(4-(oxiran-2-ylmethoxy)phenyl)(phenyl)methanone using the polymerization procedure given for 1.
Figure 3:
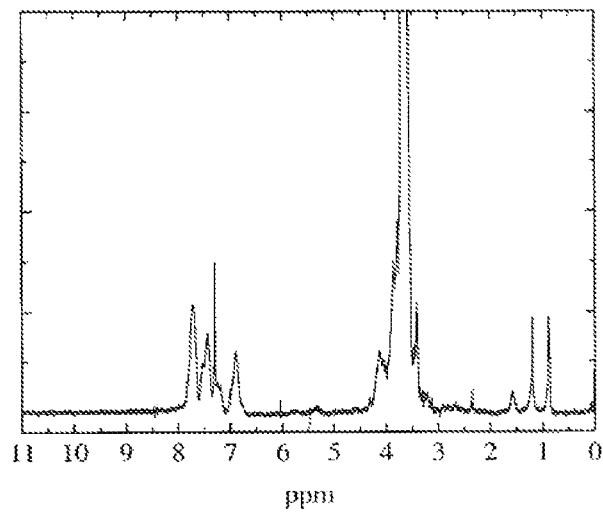
FIG. 3 shows the $^1$H-NMR spectrum of poly-co-ethyleneoxid-(4-(oxiran-2-ylmethoxy)phenyl)(phenyl)methanone using the polymerization procedure given for 2.

"Optionally-substituted" means optionally-substituted with one or more substituents selected from the group consisting of C1-C25 linear, branched or cyclic alkyl, aryl, —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates. Preferably the one or more substituents are selected from the group consisting of —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates. Most preferably, the substituent is selected from the group consisting of —OH, —CN, halogens, amines, amides, alcohols, ethers, thioethers, sulfones and derivatives thereof, sulfonic acid and derivatives thereof, and sulfoxides and derivatives thereof.

Hydrophilic

A material is described as hydrophilic if it has a natural affinity to water. Hydrophilic materials are defined as those which have a contact angle with water of less than 90°, preferably less than 80°, more preferably less than 75° and most preferably less than 50° (see ASTM D7334-08) measured with an advancing contact angle measurement. In short, the method for measuring the advancing contact angle of a water drop on a surface, is done by deposition of the water droplet (~5-20 μL) controlled in size within 0.1 μL using a hypodermic syringe. A goniometer is then adjusted such that the interior angle of each of the two points of contact of the drop can be determined. Two angle measurements (one on each drop edge) of three drops on the specimen is determined and the contact angle for the specimen is the average of these six angle measurements.

A hydrophilic polymer is likely to contain atoms with high electronegative values such as oxygen and nitrogen. Materials which are hydrophilic according to the above definition will also have an affinity for short-chain (e.g. C1-C8) alcohols and glycerol. Specific examples of hydrophilic polymers are polyethylene oxides, polyvinylacetates, polyvinylpyrolidones, amine functional polymers e.g. poly(2-ethyl-2-oxazoline), acrylics, polyethers, polyalkylethersulfonate, polyvinyl alcohols.

Hydrophilic Gels

A gel is a interconnected, rigid network with pores of submicrometer dimensions and polymeric chains whose average length is greater than a micrometer. The term "gel" is discussed in detail in Flory, P. J. Principles of Polymer Chemistry; Cornell University Press: Ithaca, N.Y., 1953; Chapter IX.

A definition of a gel is provided in Polymer Gels and Networks, 1 (1993), 5-17: A gel is a soft, solid or solid-like material of two or more components one of which is a liquid, present in substantial quantity. Solid-like gels are characterized by the absence of an equilibrium modulus, by a storage modulus, $G'(\omega)$, which exhibits a pronounced plateau extending to times at least of the order of seconds, and by a loss modulus, $G''(\omega)$, which is considerably smaller than the storage modulus in the plateau region.

In the interest of characterizing the efficiency of a photoinitiator in cross-linking polymeric matrices, the transition from a liquid to a solid material is of importance. Liquids are characterized by having $G''(\omega) > G'(\omega)$ and correspondingly, solids are characterized by $G''(\omega) < G'(\omega)$. The transition from liquid to solid, often referred to as the gel-point, is defined as when $G''(\omega) = G'(\omega)$. The cure time defined as the time from initiation of a curing process to when $G''(\omega) = G'(\omega)$ or tan δ=1 is a characteristic measure of the efficiency of a photoinitiator in a specific matrix composition.

Specific Embodiments of the Invention

The present invention provides novel catheters comprising hydrophilic gels, and methods for their manufacture. In a first aspect, the invention provides a method for manufacturing a catheter comprising a hydrophilic gel. The method comprising the steps of:

a. combining a polymeric photoinitiator of the general formula I:

$$R_1(A_1)_r\text{-}(R_2(A_2)_m\text{-O})_o\text{—}(R_3(A_3)_n\text{-O})_p\text{—}R_4(A_4)_s \qquad (I)$$

with one or more gel-forming polymers and/or gel-forming monomers to form a matrix composition, b. curing the matrix composition obtained in step a. by exposing it to UV radiation, c. exposing the matrix composition to a swelling medium, d. incorporating the hydrophilic gel/matrix composition into a catheter, wherein steps b. and c. may take place in any order, provided that, if step d. is carried out first, step b. takes place before step c. Migration of the UV active substances to the surface of the hydrophilic gel is diminished when polymeric photoinitiators are used as opposed to lower molecular weight photoinitiators.

Suitably, step b. takes place before step c. Preferred orders for the steps are a., b., d., c. and a., d., b., c.

In the polymeric photoinitiator of formula (I), $R_2$ and $R_3$ are independently at each occurrence identical or different, linear or branched alkylene or cycloalkylene groups; wherein $R_2$ and $R_3$ may be substituted with one or more substituents selected from CN; azides, esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group. $R_2$ may be —$CH_2CH_2$—, in which one or more H atoms may be replaced by $A_2$. Similarly, $R_3$ may be —$CH_2CH_2$—, in which one or more H atoms may be replaced by $A_3$. As an alternative, $R_2$=—$CH(CH_3)CH_2$—, in which one or more H atoms may be replaced by $A_2$. $R_3$ may be —$CH(CH_3)CH_2$—, in which one or more H atoms may be replaced by $A_3$.

$R_2$ and $R_3$ can be selected from any alkylene group having up to 25 carbon atoms and include both branched and straight chain alkylene groups. Exemplary, non-limiting alkylene groups include methylene, ethylene, propylene, butylene, pentylene, hexylene, heptylene, octylene, nonylene, in the normal, secondary, iso and neo attachment isomers. Exemplary, non-limiting cycloalkylene groups include cyclopropylene, cyclobutylene, cyclopentylene and cyclohexylene.

As set out above, the alkylene groups $R_2$ and $R_3$ may be substituted with, apart from the photoinitiator moieties, substituents such as CN, azides, esters, ethers, amides, halogen atoms, sulfones, sulfonic derivatives, $NH_2$ or $Nalk_2$. "alk" is any $C_1$-$C_8$ straight chain alkyl group, $C_3$-$C_8$ branched or cyclic alkyl group. Photoinitiator moieties can be covalently linked to $R_2$ and/or $R_3$ as designated by $R_2(A_2)$ and $R_3(A_3)$, where $A_2$ and $A_3$ can be any of the photoinitiator moieties described herein.

$R_1$ and $R_4$ are independently at each occurrence identical or different, linear or branched alkyl or cycloalkyl groups or aryl groups or are independently at each occurrence selected from H, OH, CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, polyethylenes, polyethylene oxides, polyvinyl pyrrolidones, polypropylenes, polyesters, polyamides, polyacrylates, polystyrenes, and polyurethanes.

In some cases, when $R_1$ and $R_4$ are alkyl and aryl groups, they may be substituted with, apart from the photoinitiator moieties, substituents such as CN, OH, azides, esters, ethers, amides (e.g. —CONR'R" or R'CONR"—, where R' and R" are alkyl groups, suitably C1-C25 alkyl groups), halogen atoms, sulfones, sulfonic derivatives, $NH_2$ or $Nalk_2$, where alk is any C1-C8 straight chain alkyl group, C3-C8 branched or cyclic alkyl group. Photoinitiator moieties can be covalently linked to $R_1$ and/or $R_4$ as designated by $R_1(A_1)$ and $R_4(A_4)$, where $A_1$ and $A_4$ can be any of the photoinitiator moieties described above.

$R_1$ and $R_4$ may independently be at each occurrence identical or different, linear or branched alkyl or cycloalkyl groups. $R_1$ and $R_4$ can be selected from any alkyl group having up to 25 carbon atoms and include both branched and straight chain alkyl groups. Exemplary, non-limiting alkyl groups include methyl, ethyl, propyl, butyl, pentyl, hexyl, heptyl, octyl, nonyl, in the normal, secondary, iso and neo attachment isomers. Exemplary, non-limiting cycloalkyl groups include cyclopropyl, cyclobutyl, cyclopentyl and cyclohexyl.

$R_1$ and $R_4$ can also be selected from aryl groups, such as any aromatic hydrocarbon with up to 20 carbon atoms. Exemplary, non-limiting aryl groups include phenyl, naphthyl, furanyl, thiophenyl, pyrrolyl, selenophenyl, and tellurophenyl. $R_1$ and $R_4$ can also be H, OH, CN, halogens, amines (e.g. —NR'R", where R' and R" are alkyl groups, suitably C1-C25 alkyl groups), amides (e.g. —CONR'R" or R'CONR"—, where R' and R" are alkyl groups, suitably C1-C25 alkyl groups), alcohols, ethers, thioethers, sulfones and derivatives thereof, sulfonic acid and derivatives thereof, sulfoxides and derivatives thereof, carbonates, isocyanates, nitrates, acrylates. $R_1$ is suitably OH. $R_4$ is suitably H.

In one aspect, $R_1$ and $R_4$=—$CH_2CH_2$—, in which one or more H atoms may be replaced by $A_1$ or $A_4$, respectively.

Furthermore, $R_1$ and $R_4$ can be selected from polymeric entities. $R_1$ and $R_4$ may each independently be selected from the group consisting of polyacrylates, polyethylene oxides, polyvinyl pyrrolidones, polyesters, polyamides and polyurethanes. The molecular weight of said polymeric entities is typically in the range of 50-50,000 Da.

The indices o and p are each a real number from 0-5000 provided that o+p>0. The indices o and p may each be from 0-3000, preferably 0-2000.

The indices m and n are each a real number from 0-10, provided that m+n>0. Suitably, m and n are each an integer of from 0-8, preferably 0-5, provided that m+n>0. More suitably, m=1 and/or n=1. Suitably, m+n≥1. In one aspect, m=1, n=0 and the ratio o:p is at least 1:1000, preferably at least 1:500.

The indices r and s are each a real number from 0-5. Suitably, r and s are each from 0-4, preferably 0-2. Suitably, r and s are independently 1 or greater, e.g. 1 or 2.

The indices m, n, o, p, r and s in the general formula I represent an average/sum and the formula I thereby represents alternating, periodic, statistical/random, block and grafted copolymers. As an example of a random copolymer may be mentioned the copolymer ABAAABABBABA having the formula $A_7B_5$.

As an example of the identity of formula I applied to a photoinitiator described in the present invention is given in Scheme 1.

Scheme 1: Example of applying formula I to a photoinitiator. Formula I then reads $HO(CH_2CH_2O)_6(CH_2CH(CH_2OPhCOPh))_2H$ or $HO(CH_2CH_{1.75}(CH_2OPhCOPh)_{0.25}O)_8H$.

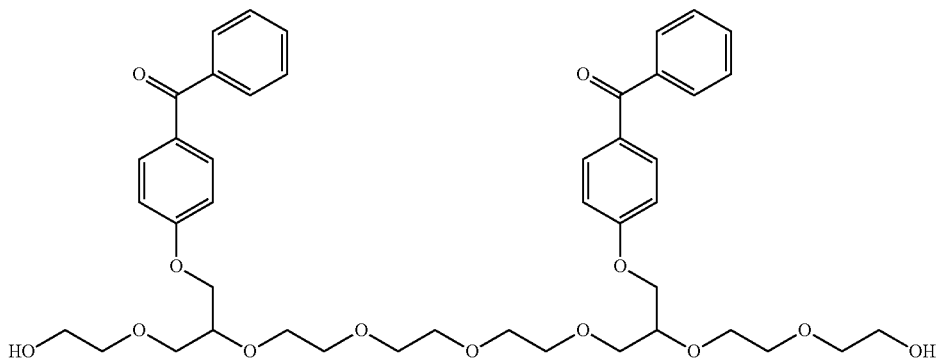

In a preferred embodiment, the polyalkylether photoinitiator according to the invention may have a molecular weight between 5 and 10,000 kDa, preferably between 10 kDa and 1,000 kDa, more preferably between 15 kDa and 500 kDa. In the present invention, $M_w$ (the weight averaged molecular weight) is used to characterize the polymeric photoinitiators.

Efficiency of the polymeric photoinitiator is among other things related to how well the photoinitiator is blended with the gel-forming polymer(s) or monomer(s). Amongst important parameters in this respect is the molecular weight of the photoinitiator. A molecular weight which is too high does not allow for good miscibility of the polymeric photoinitiator with other components of the matrix composition. Important for the present invention is the miscibility of the polymeric photoinitiator with the other components in the matrix composition, when considering a two-component system. In particular, if the chemical nature and molecular weight of the polymeric photoinitiator and the gel-forming polymer(s) are markedly different, a poor miscibility is obtained, which in turn results in a matrix composition that is difficult to cure.

Photoinitiator Moieties

In Formula (I) above, $A_1$, $A_2$, $A_3$ and $A_4$ are identical or different photoinitiator moieties.

Photoinitiator moieties $A_1$, $A_2$, $A_3$ and $A_4$ may be linked to $R_1$, $R_2$, $R_3$, and $R_4$, respectively, via a spacer group. The spacer group may be selected from the group consisting of alkylene, cycloalkylene, aryl, and alkylene ether groups. The spacer group, if any, may be selected from the same functional groups as $R'_1$, $R'_2$, $R'_3$ and $R'_4$ and additionally from groups consisting of alkylethers, such as —$(CH_2CH_2O)_t$—, where t can be any integer from 0-100.

In the present invention, a photoinitiator is defined as a moiety which, on absorption of light, generates reactive species (ions or radicals) and initiates one or several chemical reactions or transformation. One preferred property of the photoinitiator is good overlap between the UV light source spectrum and the photoinitiator absorption spectrum. Another desired property is a minor or no overlap between the photoinitiator absorption spectrum and the intrinsic combined absorption spectrum of the other components in the matrix.

In an embodiment of the polyalkylether photoinitiator according to the invention, $A_1$, $A_2$, $A_3$ and $A_4$ are identical or different photoinitiator moieties selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, silane, maleimides, and derivatives thereof. The photoinitiator moieties $A_1$, $A_2$, $A_3$ and $A_4$ can also consist of derivatives of the photoinitiator moieties listed.

In an embodiment of the polyalkylether photoinitiator according to the invention, $A_1$, $A_2$, $A_3$ and $A_4$ are identical or different photoinitiator moieties selected from the group consisting of 2-hydroxy-2-methyl-propiophenone, benzophenone, thioxanthone, benzil, anthraquionone, camphorquinone, benzoin ether, acylphosphine oxide, silane, and derivatives thereof. The photoinitiator moieties $A_1$, $A_2$, $A_3$ and $A_4$ can also consist of derivatives of the photoinitiator moieties listed.

In an embodiment of the polyalkylether photoinitiator according to the invention, $A_1$, $A_2$, $A_3$ and $A_4$ are identical photoinitiator moieties. However, $A_1$, $A_2$, $A_3$ and $A_4$ may be at least two different photoinitiator moieties.

Suitably, at least one of $A_1$, $A_2$, $A_3$ and $A_4$ is a benzophenone photoinitiator moiety. At least $A_2$ and $A_3$ may be benzophenone photoinitiator moieties.

The photoinitiator moieties of the invention may independently be cleavable (Norrish Type I) or non-cleavable (Norrish Type II). Suitably, the photoinitiator moieties of the invention are all non-cleavable (Norrish Type II). For reference, see e.g. A. Gilbert, J. Baggott: "Essentials of Molecular Photochemistry", Blackwell, London, 1991. Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Non-cleavable photoinitiator moieties do not break down upon excitation, thus providing fewer possibilities for the leaching of small molecules from the matrix composition. The photoinitiator moieties of the invention are efficient in transforming light from the UV or visible light source to reactive radicals which can abstract hydrogen atoms and other labile atoms from polymers and hence effect covalent cross-linking. Optionally, amines, thiols and other electron donors can be either covalently linked to the polymeric photoinitiator or added separately or both. The addition of electron donors is not required but may enhance the overall efficiency of cleavable photoinitiators according to a mechanism similar to that described for the non-cleavable photoinitiators below.

Excited non-cleavable photoinitiators do not break down to radicals upon excitation, but abstract a hydrogen atom from an organic molecule or, more efficiently, abstract an electron from an electron donor (such as an amine or a thiol). The electron transfer produces a radical anion on the photoinitiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones and related ketones such as thioxanthones, xanthones, anthraquinones, fluorenones, dibenzosuberones, benzils, and phenyl ketocoumarins are important examples of non-cleavable photoinitiators. Most amines with a C—H bond in α-position to the nitrogen atom and many thiols will work as electron donors. The photoinitiator moieties of the invention are preferably non-cleavable.

Self-initiating photoinitiator moieties are within the scope of the present invention. Upon UV or visible light excitation, such photoinitiators predominantly cleave by a Norrish type I mechanism and cross-link further without any conventional photoinitiator present, allowing thick layers to be cured. Recently, a new class of β-keto ester based photoinitiators has been introduced by M. L Gould, S. Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz. After base-catalyzed Michael addition of the ester to polyfunctional acrylates, a network is formed with a number of quaternary carbon atoms, each with two neighbouring carbonyl groups.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photoinitiators and at the same time spontaneously polymerize by radical addition across the maleimide double bond. In addition, the strong UV absorption of the maleimide disappears in the polymer, i.e. maleimide is a photobleaching photoinitiator; this could make it possible to cure thick layers.

So, in an embodiment of the invention, the photoinitiator moieties include at least two different types of photoinitiator moieties. Preferably, the absorbance peaks of the different photoinitiators are at different wavelengths, so the total amount of light absorbed by the system increases. The different photoinitiators may be all cleavable, all non-cleavable, or a mixture of cleavable and non-cleavable. A blend of several photoinitiator moieties may exhibit synergistic properties, as is e.g. described by J. P. Fouassier: "Excited-State Reactivity in Radical Polymerization Photoinitiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethyl-amino) benzophenone+benzophenone], [benzophenone+2,4,6-trimethylbenzophenone], [thioxanthone+methylthiophenyl morpholinoalkyl ketone].

Furthermore, it has recently been found that covalently linked 2-hydroxy-1-(4-(2-hydroxyethoxy)phenyl)-2-methyl-propan-1-one, which is commercially available with the trade name Irgacure 2959, and benzophenone in the molecule 4-(4-benzoylphenoxyethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20, 2005, vol. 2, p. 375-81, Vincentz. This shows that different photoinitiator moieties may show significant synergistic effects when they are present in the same oligomer or polymer. Such covalently linked photoinitiator moieties are also applicable within the present invention.

Each and every one of the above-discussed types of photoinitiators and photoinitiator moieties may be utilised as photoinitiator moieties in the polymeric photoinitiators of the present invention.

Polymeric Backbone (Photoinitiator Segment)

The polymeric backbone consists of a polyalkylether segment with the general formula —$(R_2(A_2)_m$-O$)_o$—$(R_3(A_3)_n$-O$)_p$—, wherein $R_2$ and $R_3$ and can be selected from any alkylene group having up to 25 carbon atoms and include both branched and straight chain alkylene and cycloalkylene groups. Exemplary, non-limiting alkylene groups include methylene, ethylene, propylene, butylene, pentylene, hexylene, heptylene, octylene, nonylene, in the normal, secondary, iso and neo attachment isomers. Exemplary, non-limiting cycloalkylene groups include cyclopropylene, cyclobutylene, cyclopentylene and cyclohexylene.

In an embodiment of the polyalkylether photoinitiator according to the invention $R_2$ and $R_3$ are independently —$CH_2CH_2$— in which one or more H atoms may be replaced by $A_2$ or $A_3$, respectively. Suitably, $R_2$ and $R_3$ are both —$CH_2CH_2$— in which one or more H atoms may be replaced by $A_2$ or $A_3$, respectively. When $R_2$ and $R_3$ are —$CH_2CH_2$—, gel formation is promoted. In particular, gel formation is promoted when $R_1$, $R_2$, $R_3$ and $R_4$ are all —$CH_2CH_2$— in which one or more H atoms may be replaced by $A_1$, $A_2$, $A_3$ or $A_4$ respectively.

In an embodiment of the polyalkylether photoinitiator according to the invention $R_2$ and $R_3$ are independently —CH($CH_3$)$CH_2$— in which one or more H atoms may be replaced by $A_2$ or $A_3$, respectively.

In some cases the alkylene groups may, apart from the photoinitiator moieties, bear substituents such as CN, azides, esters, ethers, amides (e.g. —CONR'R" or R'CONR"—, where R' and R" are alkyl groups, suitably C1-C25 alkyl groups), halogen atoms, sulfones, sulfonic derivatives, $NH_2$ or $Nalk_2$, where alk is any C1-C8 straight chain alkyl group, C3-C8 branched or cyclic alkyl group. Photoinitiator moieties can be covalently linked to $R_2$ and/or $R_3$ as designated by $R_2(A_2)_m$ and $R_3(A_3)_n$, where $A_2$ and $A_3$ can be any of the photoinitiator moieties described above. The indices m, n, o and p are as set out above.

Polymeric Photoinitiators of the Invention
Polyethylene Oxide Derived Photoinitiators The polymeric photoinitiators can be either synthesized by a polymerization reaction or photoinitiators can be grafted onto a polymeric backbone. A general scheme for a direct synthesis of a polymeric photoinitiator with pendant photoinitiator moieties based on epoxy-ring opening is shown in Scheme 2, where the symbols from the general formula for the polymeric photoinitiators are exemplified.

Scheme 2: General method of preparing random copolymers of epoxide functionalized photoinitiators with substituted epoxides. The solid dotted line represents that under specific reaction conditions, this position is primarily substituted with the photoinitiator system. Other reactions might result mainly in substitution at the position labelled with a dashed line.

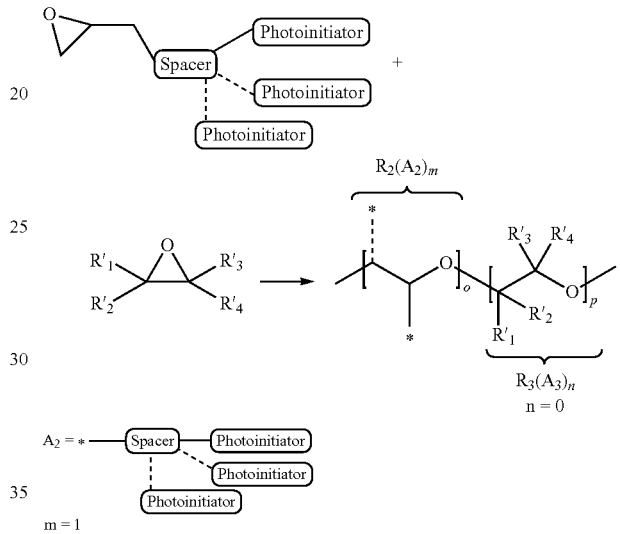

The epoxide functionality used for the polymerization is obtained through a reaction with epichlorhydrine, but might also be obtained through a reaction with an allyl-derivative which is then subsequently oxidized with an oxidizing agent such as m-chloro-perbenzoic acid or hydrogen peroxide.

As illustrated in Scheme 2, attack of a nucleophile, either the initiator or an alkoxide ion, occurs at the least substituted carbon atom on the epoxide present on the spacer group. Some reaction conditions, e.g. acidic conditions might favour the converse meaning that the most substituted carbon atom on the epoxide is attacked by the nucleophile. For simplicity, only polymerizations resulting in attack of the least substituted carbon atom in the photoinitiator attached epoxide, is illustrated in the following, but the invention is not so limited.

With respect to substituents, $R'_1$, $R'_2$, $R'_3$ and $R'_4$ can be selected from any alkyl groups having up to 25 carbon atoms and includes both branched, cyclic and straight chain alkyl groups. Exemplary alkyl groups include methyl, ethyl, propyl, butyl, pentyl, hexyl, heptyl, octyl, nonyl, in the normal, secondary, iso and neo attachment isomers. $R'_1$, $R'_2$, $R'_3$ and $R'_4$ can also be selected from aryl groups, such as any aromatic hydrocarbon with up to 20 carbon atoms. Exemplary aryl groups include phenyl, naphthyl, furanyl, thiophenyl, pyrrolyl, selenophenyl, and tellurophenyl. In some cases, the alkyl and aryl groups may bear substituents such as CN, azides, esters, ethers, amides (e.g. —CONR'R" or R'CONR"—, where R' and R" are alkyl groups, suitably C1-C25 alkyl groups), halogen atoms, sulfones, sulfonic derivatives, $NH_2$ or $Nalk_2$, where alk is any C1-C8 straight chain alkyl group, C3-C8 branched or cyclic alkyl group. $R'_1$, $R'_2$, $R'_3$ and $R'_4$ may also be H.

As a first example, a polymerization of 2-hydroxy-2-methyl-1-(4-(2-(oxiran-2-ylmethoxy)ethoxy)phenyl)propan-1-one (3) with either itself or ethylene oxide results in a (co)-polymer which is a polymeric photoinitiator (Scheme 3). The precursor for the synthesis of this polymer is 2-hydroxy-1-(4-(2-hydroxyethoxy)phenyl)-2-methylpropan-1-one (Irgacure 2959). A synthesis of (3) is outlined in U.S. Pat. No. 5,744,512.

Scheme 3: Preparation of polymeric photoinitiator from Irgacure 2959.

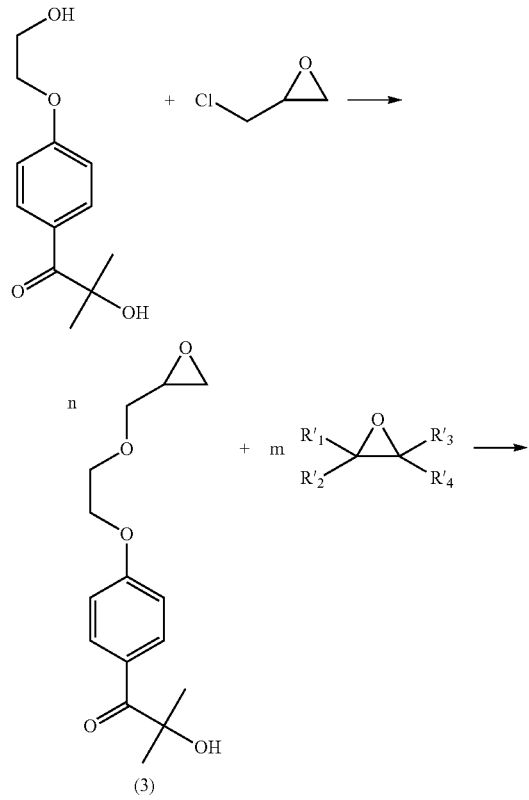

(3)

An alternate route to analogues of (3) is illustrated in Scheme 4, where the hydroxyalkyl phenone is formed in a Friedel-Crafts reaction with isobutyryl chloride as described in U.S. Pat. No. 5,744,512.

Scheme 4: Preparation of analogues of (3).

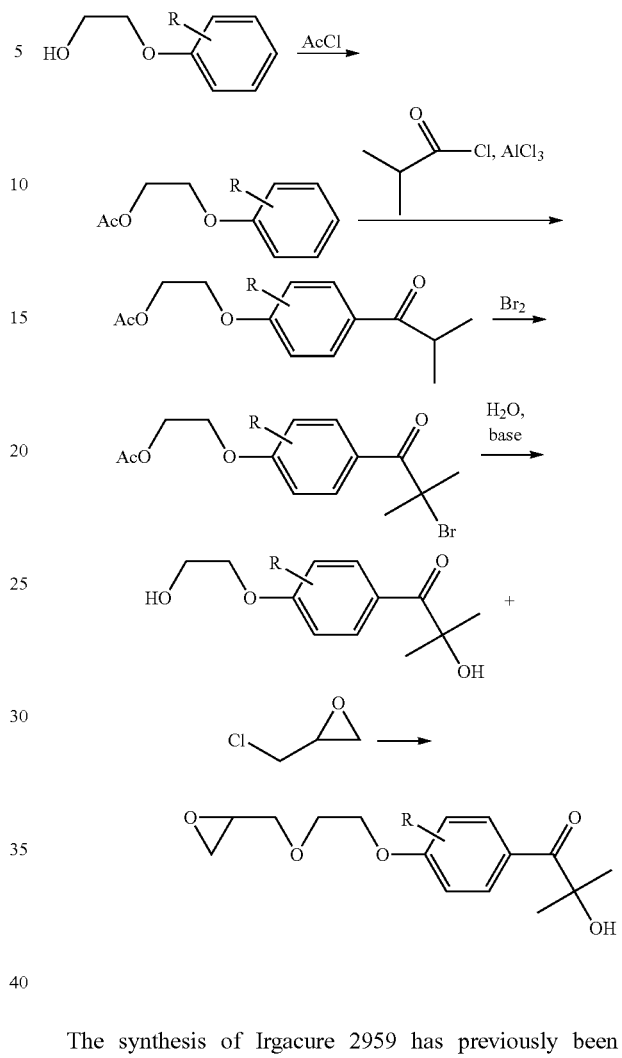

The synthesis of Irgacure 2959 has previously been described elsewhere (German Offenlegungsschrift 3.512.179). The attachment of photoinitiators with similar structure as Irgacure 2959 onto a polyalkylether is the main focus of the present invention. Following the synthetic route in Scheme 4, it will be possible to place specific substituents on the benzene ring by methods generally known in the art.

Derivatives of Irgacure 2959 are characterized as Type I photoinitiators, and other photoinitiators that fall in this category are benzoinethers, benzil ketals, α-dialkoxy-acetophenones, α-hydroxy-alkyl-phenones, α-amino-alkyl-phenones and acyl-phosphine oxides. As a further example of a polymeric photoinitiator based on a benzoinether, Scheme 5: Preparation of an epoxide substituted benzoinether, which is polymerized with a substituted epoxide.

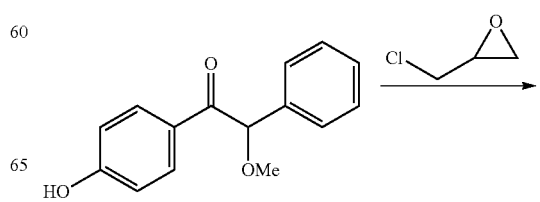

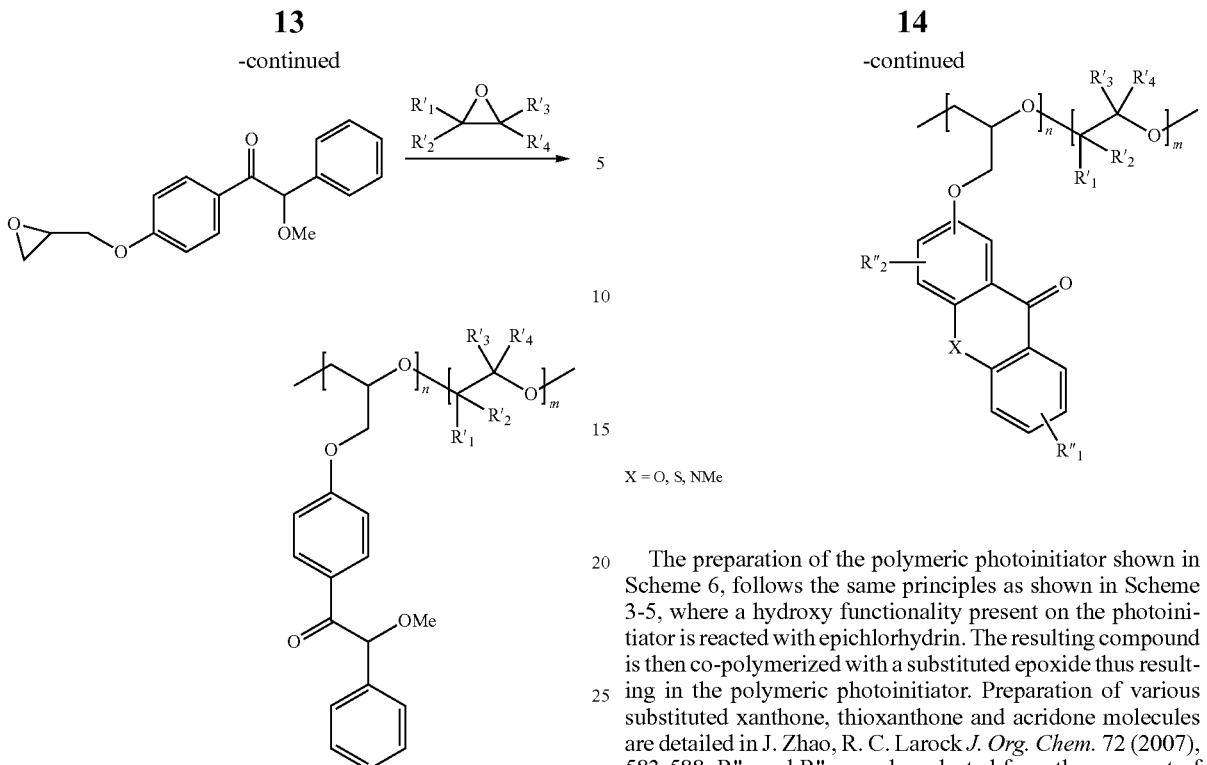

Depicted in Scheme 3-5 are examples of Type I photoinitiators attached to a polyalkylether backbone and an example of the preparation of a Type II polymeric photoinitiator is shown in Scheme 6 with xanthones, thioxanthones and acridones as the photoinitiator moiety itself.

Scheme 6: Preparation of xanthone, thioxanthone and acridone substituted polymeric photoinitiators.

X = O, S, NMe

The preparation of the polymeric photoinitiator shown in Scheme 6, follows the same principles as shown in Scheme 3-5, where a hydroxy functionality present on the photoinitiator is reacted with epichlorhydrin. The resulting compound is then co-polymerized with a substituted epoxide thus resulting in the polymeric photoinitiator. Preparation of various substituted xanthone, thioxanthone and acridone molecules are detailed in J. Zhao, R. C. Larock *J. Org. Chem.* 72 (2007), 583-588. $R''_1$ and $R''_2$ may be selected from the same set of functional groups as $R'_1$, $R'_2$, $R'_3$ and $R'_4$.

As another example of a type II polymeric photoinitiator, a benzophenone substituted polyethylene oxide is illustrated in Scheme 7.

Scheme 7: Synthesis of a benzophenone substituted polyethylene oxide.

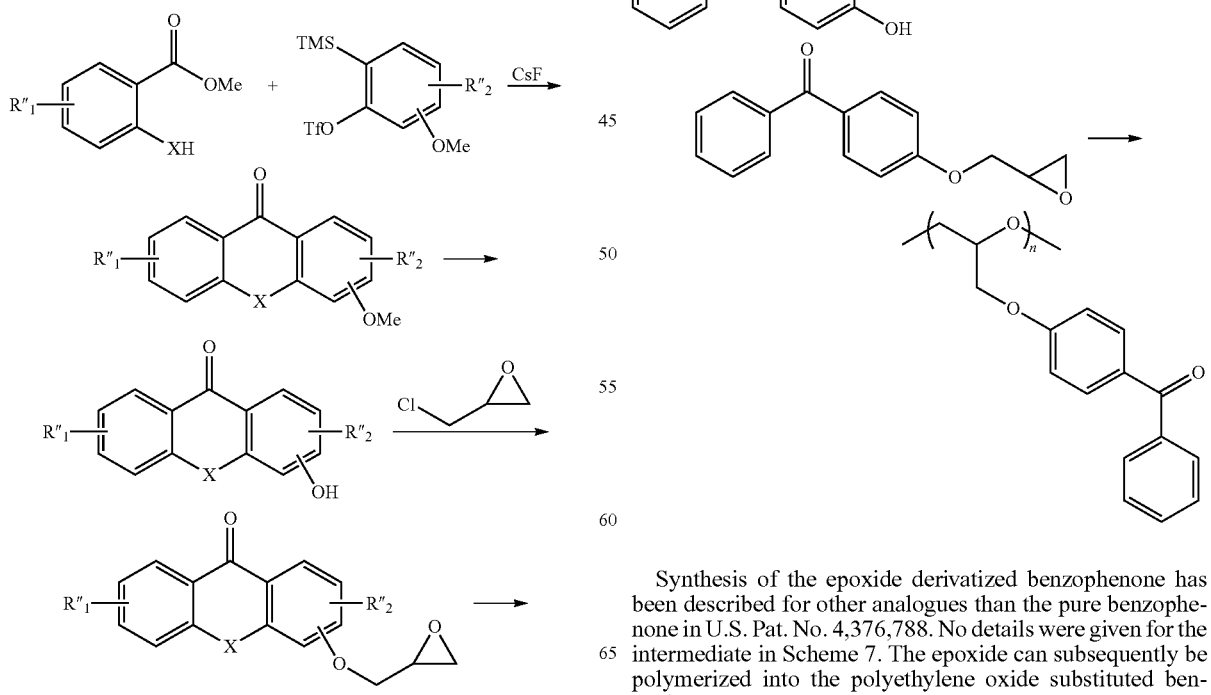

Synthesis of the epoxide derivatized benzophenone has been described for other analogues than the pure benzophenone in U.S. Pat. No. 4,376,788. No details were given for the intermediate in Scheme 7. The epoxide can subsequently be polymerized into the polyethylene oxide substituted benzophenone.

An alternate route to derivatized polyethylene oxide could be via grafting techniques as exemplified in Scheme 8.

Scheme 8: Grafting of a peroxy benzophenone ester onto polyethylene oxide.

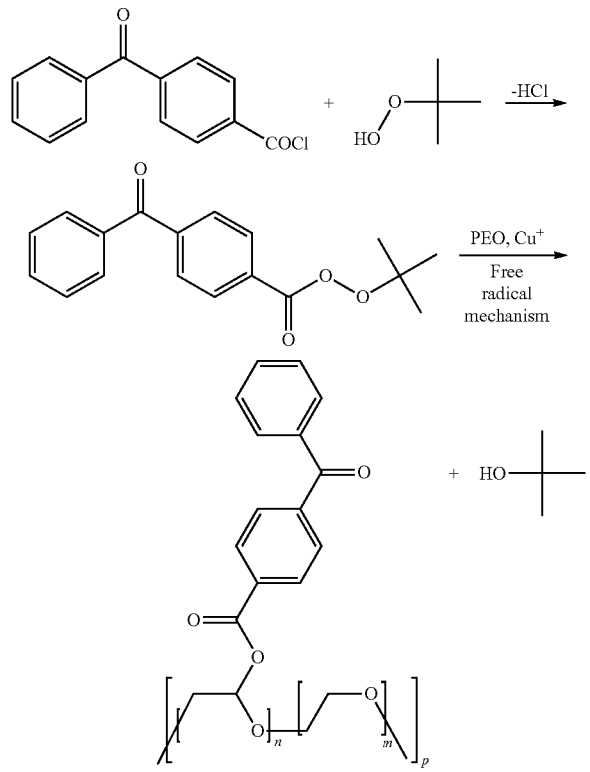

Grafting of the peroxy ester is catalysed by copper(I) as described in J. March: "Advanced Organic Chemistry. Reaction, Mechanisms, and Structure", 3. ed., p. 636-7, Wiley-Interscience, New York, 1985). The specific example shown in Scheme 8 is also disclosed in WO2008071796.

Polyalkyl Oxide Derived Photoinitiators

A general scheme for preparation of polyalkyl oxide derived photoinitiators is shown in Scheme 9, where the polymer is synthesized through an acyclic diene polymerization (ADMET) reaction.

Scheme 9: ADMET polymerization of dienes and subsequent hydrogenation for forming a polyalkyl ether based photoinitiator. m', n', o', m'', n'', o'', p' and q' can be any integers 0-10000.

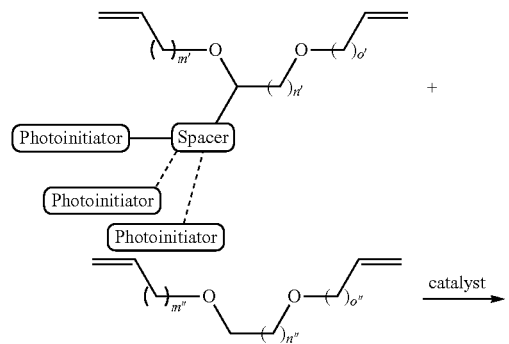

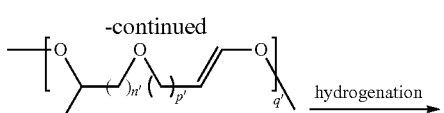

Such polymerization types have been described in K. B. Wagener, K. Brzezinska *Macromolecules*, 24 (1991), 5273-5277.

Considerable research has been focused on polymerizing substituted oxiranes, with different initiators and different solvents. Thus (4-(oxiran-2-ylmethoxy)phenyl)(phenyl)methanone can most likely be polymerized with e.g. potassium t-butoxide as an initiator in a anionic polymerization scheme as done in P. Yang, X. Zhu, Y. Yo, Y. M. Xia and T. Li *Jour. Appl. Polym. Sci.* 113 (2009), 3656-3660. Reaction conditions for similar polymerizations with a variety of other nucleophiles such as potassium hydroxide as initiators are presented in J. Cao, N.- F. Yang, P.- D. Wang and L.- W. Yang *Polymer International*, 57 (2008), 530-537. Several reaction conditions are published in patent literature as well, where in U.S. Pat. No. 4,472,560 metal cyanide complexes are used as catalysts for the epoxide polymerization. Organoaluminium catalysts are also described in U.S. Pat. No. 4,009,128 to work well in a cationic polymerization scheme.

Matrix Composition

In one embodiment, the polymeric photoinitiators of formula (I) are combined with one or more gel-forming polymers and/or gel-forming monomers to form a matrix composition. Gel-forming polymers are polymers which—due to their hydrophilic nature—retain a swelling medium such as water within the polymer structure, allowing a hydrophilic gel to be formed, once the matrix composition is cured.

In particular, the gel-forming polymer may be a hydrogel-forming polymer. A hydrogel-forming polymer is selected from the group comprising polyacrylates, polyalkylethers such as polyethylene oxide, polyurethanes, polyamides, polyethylene vinyl acetates, polyvinylpyrrolidone and co-polymers and blends thereof. Preferably, the hydrogel-forming polymer is selected from the group consisting of polyalkylethers, polyurethanes, polyethylene vinyl acetate.

A gel-forming monomer is a monomer which produces a gel-forming polymer when polymerised. A hydrogel-forming monomer is one which produces hydrophilic polymers as set out above. Suitable hydrogel-forming monomers may be selected from the group consisting of acrylate monomers, N-vinylpyrrolidone, and epoxide monomers and, for example, monomers with two or more hydroxyl and/or amino functionalities, such as diethanol and aminoethanol.

For providing a gel after a curing step, a polymerization of the monomeric entities occurs in conjecture with cross-linking. After the curing step, the cross-linked composition is then swelled with a swelling medium such as water, C1-05 alcohols, glycerol and polyethylene glycol (PEG), preferably PEG-2000.

Other possible components in the matrix composition include anti-oxidants such as BHT (2,6-bis(1,1-dimethylethyl)-4-methylphenol), Irganox 1010 (from Ciba) and similar structures. Therapeutic additives are also possible components in the matrix composition. When such additional components are present in the matrix composition, they may be added directly at the same time as the matrix composition is formed, at any point prior to curing, or as a component of the swelling medium. The latter is most preferred.

Curing

Once the polymeric photoinitiator of the general formula I has been combined with one or more gel-forming polymers and/or gel-forming monomers to form a matrix composition in the method of the invention, the matrix composition is cured by exposing it to UV radiation.

Curing can either occur in the molten state, or in a solution. The latter comprises steps, where the matrix composition is dissolved in a suitable solvent and for example spray-coated on to a tube, and subsequently exposed to UV radiation. The solvent can afterwards either be evaporated or remain in the coating and function as a swelling medium to provide the desired gel.

The ultraviolet spectrum is divided into A, B and C segments where UV A extends from 400 nm to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelengths. In particular, scattering phenomena are less pronounced at longer wavelength, thus giving a larger penetration depth in the material. Thus photoinitiators which absorb, and can induce curing, at longer wavelength are of interest. By judicially choosing substituents on the aromatic moieties, the absorption spectrum of the polymeric photoinitiator can to some extent be red-shifted, which would then facilitate curing at comparatively greater depths.

Multi-photon absorption can also be used to cure samples using light sources emitting at wavelengths twice or even multiple times the wavelength of light needed for curing in a one-photon process. For example, a composition containing a photoinitiator with an absorption maximum at ~250 nm could possibly be cured with a light source emitting at ~500 nm utilizing a two-photon absorption process provided that the two-absorption cross section is sufficiently high. A multi-photon initiated cure process could also facilitate greater spatial resolution with respect to the cured area, exemplified in Nature 412 (2001), 697 where a 3D structure is formed by a two-photon curing process.

In the present invention, curing is primarily initiated by exposing the matrix composition or polymeric photoinitiator to high energy irradiation, preferably UV light. The photoinitiated process takes place by methods described above and which are known per se, through irradiation with light or UV irradiation in the wavelength range from 250 to 500 nm. Irradiation sources which may be used are sunlight or artificial lamps or lasers. Mercury high-pressure, medium pressure or low-pressure lamps and xenon and tungsten lamps, for example, are advantageous. Similarly, excimer, solid stated and diode based lasers are advantageous. Even pulsed laser systems can be considered applicable for the present invention. Diode based light sources in general are advantageous for initiating the chemical reactions.

In the curing process the polymeric photoinitiator transforms the matrix composition, in a chemical process induced by light.

Gel-State

To provide the gel of the invention, the matrix composition is exposed to a swelling medium such as water, C1-05 alcohols, glycerol and polyethylene glycol (PEG), preferably PEG-2000. The compositions are thus swelled to provide a gel. Contact with the swelling medium may take place before or after curing of the matrix composition. The swelling medium may be in its pristine state, or present in combination with other substances, e.g. in a saline solution or a body fluid. Species present in the gaseous state in equilibrium with a significant portion present in their liquid form also constitute a swelling medium. The invention thus provides a method for the manufacture of a hydrophilic gel, said method comprising steps a. and b. above.

The matrix composition may be cured by exposure to UV before or after exposure to the swelling medium. If cured first, a "dry", cured matrix composition (=gel precursor) is obtained. If exposed to swelling medium first, a hydrophilic gel can be provided in a one-step process, as the curing step takes place in the presence of the swelling medium. In other words, the swelling medium for the hydrophilic gel is the solvent for the curing step. The method of the invention therefore comprises the further step of: c. exposing the matrix composition to a swelling medium. Step c. may take place before or after step b. Suitably, step c takes place before step b.

A gel is characterized as a swellable material, however, insoluble in the swelling medium. By hydrogel is meant a material comprised mainly of a water soluble or water swellable material. The gel material is characterized in terms of its rheological properties and in its dry state. In particular, the storage and the loss modulus are used to characterize the mechanical properties of the materials (T. G. Mezger: "The Rheology Handbook", Vincentz Network, Hannover, 2006). As described above, curing of a matrix composition is followed by monitoring the change of $G'(\omega)$ and $G''(\omega)$ as a function of UV exposure time. In the examples used to describe the present invention, a frequency of 1 Hz is used to probe the rheological properties and further the samples were heated to 120° C. during testing.

The invention also relates to a gel obtainable via this method, in particular a hydrophilic gel.

The polymeric photoinitiators described here can both facilitate curing of a surrounding matrix but since the photoinitiators themselves are polymers they can also "auto-cure", meaning that the polymeric photoinitiators can solely constitute a composition that is cured upon UV irradiation. As such the pristine polymeric photoinitiator can be cured to form cross-linked network, or the polymeric photoinitiator can be a constituent in a mixture which is subsequently cured to form a cross-linked network. This is particularly relevant when $R_1$ and $R_4$ are hydrophilic polymers such as e.g. polyacrylates, polyethylene oxides, polyvinyl pyrrolidones, polyesters, polyamides and polyurethanes.

The invention therefore provides a method for the manufacture of a gel precursor, said method comprising the steps of:

a. providing a polymeric photoinitiator of the general formula I:

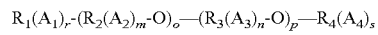

$$R_1(A_1)_r\text{-}(R_2(A_2)_m\text{-}O)_o\text{-}(R_3(A_3)_n\text{-}O)_p\text{-}R_4(A_4)_s \qquad I$$

wherein $R_2$ and $R_3$ are independently at each occurrence identical or different, linear or branched alkylene or cycloalkylene groups; wherein $R_2$ and $R_3$ may be substituted with one or more substituents selected from CN; azides, esters; ethers; amides; halogen atoms; sulfones; sulfonic derivatives; $NH_2$ or $Nalk_2$, where alk is any $C_1\text{-}C_8$ straight chain alkyl group, $C_3\text{-}C_8$ branched or cyclic alkyl group;

$R_1$ and $R_4$ are independently at each occurrence identical or different, linear or branched alkyl or cycloalkyl groups or aryl groups or are independently at each occurrence selected from H, OH, CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, polyethylenes, polyethylene oxides, polyvinyl pyrrolidones, polypropylenes, polyesters, polyamides, polyacrylates, polystyrenes, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;

o and p are each a real number from 0-5000 provided that o+p>0;

m and n are each a real number from 0-10, provided that m+n>0;

r and s are each a real number from 0-5; and $A_1$, $A_2$, $A_3$ and $A_4$ are identical or different photoinitiator moieties; and b. exposing the polymeric photoinitiator from step a. to UV radiation.

To form a hydrophilic gel from the gel precursor, steps a. and b. above are carried out, together with the additional step of:

c. exposing the polymeric photoinitiator to a swelling medium.

Steps b. and c. may take place in any order.

The "auto-curing" method for making the gel precursor suitably takes place with steps a. and b. in order, directly after one another (i.e. with no intermediate steps).

The "auto-curing" method for making the hydrophilic gel suitably takes place with steps a., b. and c. in order, directly after one another (i.e. with no intermediate steps). In one aspect of this "auto-curing" method, the method consists of steps a. b. and c.

A one-component system—as provided by the "auto-curing" method—provides advantages, in that the polymeric photoinitiators are thermoplastic. As such, they become less viscous under higher shear rate, making them easier to process in an extrusion process. In contrast, for example, polyvinyl pyrrolidone cannot be extruded. All details and structural refinements of the polymeric photoinitiator provided herein are aimed at providing photoinitiators suitable for use in the "auto-curing" method.

In addition, the polymeric photoinitiators of the "auto-curing" method may comprise the sole component of the matrix composition; i.e. the matrix composition may consist of the polymeric photoinitiators. This provides the advantage that additives (e.g. plasticizers, viscosity modifiers) can be avoided, thereby reducing the chances of low molecular weight components from leaching from the cross-linked matrix composition.

As above, the swelling medium is suitably selected from the group consisting of water, C1-05 alcohols, glycerol and polyethylene glycol (PEG), preferably PEG-2000. Most suitably, the swelling medium comprises water, and the hydrophilic gel thus produced is a hydrogel.

In the "auto-curing" method, the polymeric photoinitiator may be cured by exposure to UV before or after exposure to the swelling medium. If cured first, a "dry", cured polymeric photoinitiator is obtained. If exposed to swelling medium first, a hydrophilic gel can be provided in a one-step process, as the curing step takes place in the presence of the swelling medium. In other words, the swelling medium for the hydrophilic gel is the solvent for the curing step. Suitably, step c takes place before step b.

The invention also relates to a gel precursor and a hydrophilic gel, obtainable via the methods described herein.

Medical Device

One aspect of the invention provides a medical device comprising the gel precursor or hydrophilic gel resulting from the "auto curing" method above. The term "medical device" should be interpreted in a fairly broad sense. Suitable examples of medical devices (including instruments) are catheters (such as urinary catheters), endoscopes, laryngoscopes, tubes for feeding, tubes for drainage, endotracheal tubes, guide wires, sutures, cannulas, needles, thermometers, condoms, urisheaths, barrier coatings e.g. for gloves, stents and other implants, contact lenses, extra corporeal blood conduits, membranes e.g. for dialysis, blood filters, devices for circulatory assistance, dressings for wound care, and ostomy bags. Most relevant are catheters, endoscopes, laryngoscopes, tubes for feeding, tubes for drainage, guide wires, sutures, and stents and other implants. Particularly interesting medical devices within the context of the present invention are catheters, such as urinary catheters.

The medical device may be coated on at least a surface portion thereof with the gel precursor or hydrophilic gel described herein. In some embodiments, the hydrophilic gel covers the full (outer) surface of the medical device, and in some other embodiments, only to a part of the surface thereof. In the most relevant embodiments, the hydrophilic gel covers at least a part of the surface (preferably the whole surface) of the medical device that—upon proper use—comes into direct contact with body parts for which the medical device is intended. It may be that the medical device is coated with a gel precursor and the hydrophilic gel is generated upon contact with liquid—either the bodily fluids of the patient, or an activating solution containing water.

The invention thus provides a catheter obtainable via the method of the invention, in particular a catheter, wherein the hydrophilic gel is coated on at least a surface portion thereof.

EXAMPLES

Example 1

Synthesis of (4-(oxiran-2-ylmethoxy)phenyl)(phenyl)methanone

A solution of 4-hydroxy-benzophenone (15.02 g, 75.78 mmol) was dissolved in ethanol (75 mL) and NaOMe (4.11 g, 76.09 mmol) in methanol (75 mL) was added. The reaction mixture was stirred for 20 min at room temperature and then concentrated by evaporation on a rotavapor. The residue was dissolved in dimethylformamide (150 mL) and epichlorohydrin (10.73 g, 116 mmol) was added. After stirring for 4 hours at 110° C. and a crude product was obtained by adding activated charcoal, filtering and removal of the solvent. The crude product was recrystallized from ethanol leaving a white compound (12 g) in 62% yield. $^1$H-NMR(CDCl$_3$, RT, 300 MHz): 7.81 (d, 2H, J=9 Hz), 7.74 (d, 2H, J=7 Hz), 7.55 (t, 1H, J=8 Hz), 7.45 (t, 2H, J=7 Hz), 6.97 (d, 2H, J=9 Hz), 4.32 (dd, 1H, $J_1$=11 Hz, $J_2$=3 Hz), 3.99 (dd, 1H, $J_1$=11 Hz, $J_2$=6 Hz), 3.37 (m, 1H), 2.91 (t, 1H, J=5 Hz), 2.76 (dd, 1H, $J_1$=5 Hz, $J_2$=3 Hz); $^{13}$C-NMR (CDCl$_3$, RT, 75 MHz): 195.4, 161.9, 138.0, 132.4, 131.9, 130.5, 129.6, 128.1, 114.1, 68.8, 49.8, 44.5.

Polymerization Example 1

Synthesis of poly-co-ethyleneoxid-(4-(oxiran-2-ylmethoxy)phenyl)(phenyl)methanone Prior to the polymerization, (4-(oxiran-2 ylmethoxy)phenyl)(phenyl)methanone was carefully dried under vacuum and then transferred into a dry round bottom flask under nitrogen. The initiator for the polymerization was prepared by condensing dry THF into a round bottom flask. Naphthalene and potassium were dissolved under argon atmosphere and the solution was stirred for one day giving a dark green solution. Biphenyl methane was added and the resulting solution stirred for three days giving a deep red initiator solution.

The glassware used for the polymerization was dried thoroughly and assembled in a nitrogen glove box. When attached to the synthesis setup the glassware was flushed with argon several times prior to use. The ethylene oxide was condensed from a pressured can into a round bottom flask and dried intensively.

(4-(oxiran-2 ylmethoxy)phenyl)(phenyl)methanone (0.8 g, 3 mmol) was weighed into a reaction flask under nitrogen and the flask was dried over sodium-potassium alloy for at least 24 hours. THF (250 mL) was condensed into a reaction flask followed by ethylene oxide (11.1 g, 0.252 mol). Afterwards the initiator solution was added with an argon rinsed syringe. The reaction flask was set into a 60° C. thermostated water bath for 3-5 days. If a precipitate had formed during the reaction it was filtered from the reaction solution. The reaction solution was concentrated by taking off a part of the reaction solvent by reduced pressure. The polymer (1) was precipitated from cold diethyl ether and dried at 40° C. for at least 24 hours. Yield: 32 wt %. MW 34000, PD 1.5 (as determined by GPC). $^1$H-NMR (CDCl$_3$, 300 K, 500 MHz): 7.85-7.79 (m, 2H), 7.78-7.73 (m, 2H), 7.61-7.53 (m, 1H), 7.51-7.43 (m, 2H), 7.02-6.95 (m, 2H), 4.24-4.18 (m, 2H), 3.93-3.82 (m, 4H), 3.80-3.35 (m, 243H). The ratio of benzophenone to ethylene oxide is thus ~1:61.

Polymerization Example 2

Synthesis of poly-co-ethyleneoxid-(4-(oxiran-2-yl-methoxy)phenyl)(phenyl)methanone The bench-scale polymerizations were carried out in 250 ml glass reactor by using tri-isobutylaluminium and potassium t-butoxide as the catalyst system (see the used standard polymerization conditions in the following table).

| Parameter | Value |
|---|---|
| Process type | Slurry |
| Solvent | Toluene |
| Monomer | Ethylene oxide, 4-(oxiran-2-ylmethoxy)phenyl)(phenyl)methanone |
| Monomer feed type | Stepwise, by volume |
| Temperature (° C.) | 20 |
| Total Pressure (bar) | 0.3-0.8 |

The catalyst synthesis and polymerizations of ethylene oxide were done by using a procedure in EP1566397.
A 250 ml glass reactor was used.
Work was done in every step under inert conditions under a nitrogen atmosphere; the final polymer is also stored under nitrogen (which has not been in contact with air/water).
The addition of ethylene oxide was done by using a 100 ml sight-glass by using liquid ethylene oxide (under pressure).
The final polymer was washed with hexane, filtered and dried under reduced pressure at room temperature.
A polymerization was performed using toluene (60 mL), potassium t-butoxide (56 mg), triisobutyl aluminium (1 M in hexane, 1.4 mL), ethylene gas (26 g) and 4-(oxiran-2-yl-methoxy)phenyl)(phenyl)methanone (1.3 g). The yield of the reaction was 9.1 g of the target polymer (2). $^1$H-NMR (CDCl$_3$, 300 K, 300 MHz): 7.94-6.64 (m, 9H), 4.30-3.00 (m, 121H). The ratio of benzophenone to ethylene oxide is thus ~1:29.

Curing Example

Curing of poly-co-ethyleneoxid-(4-(oxiran-2-yl-methoxy)phenyl)(phenyl)methanone from example 1

Figure 4:
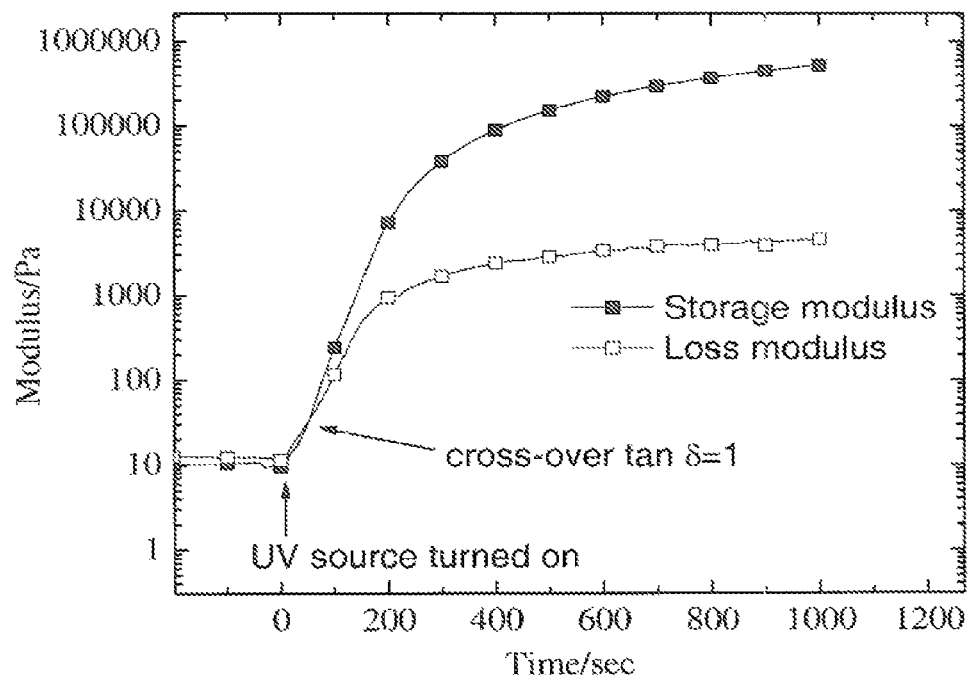
FIG. 4 shows the curing profile for pristine poly-co-ethyleneoxid-(4-(oxiran-2-ylmethoxy)phenyl)(phenyl)methanone (1) at 120° C.

An oblate of pristine poly-co-ethyleneoxid-(4-(oxiran-2 ylmethoxy)phenyl)(phenyl) methanone (1) was placed between the two plates in a rheometer (parallel plate configuration, bottom plate is a quartz glass plate). The distance between the plates was set to 0.3 mm and the temperature to 120° C. The measurements were run with a fixed strain of 1% and a constant frequency of 1 Hz. When the loss and storage modules had stabilized, a UV-lamp was turned on, thus irradiating the sample through the bottom plate on the rheometer via a fibre from the lamp. The loss and storage modules were then followed as a function of time, while the UV-lamp irradiated the sample. An illustrative result of such a measurement is shown in FIG. 4.

The comparatively low moduli prior to irradiation with UV light indicate a low viscosity in accordance with a fairly low molecular weight of the polymer of ~20 kDa. However, the loss modulus is larger than the storage modulus showing liquid behaviour of the melt. When the UV source is turned on, the moduli increase, suggesting that cross-linking reactions are initiated which forms a covalently-bonded network of polyethylene oxide chains. Eventually, the storage modulus becomes larger than the loss modulus showing that a solid or gel has formed as a result of the curing reaction. As a visual inspection, the cross-linked polyethylene oxide oblate was placed in water which resulted in a swelled gel.

Curing Example

Curing of poly-co-ethyleneoxid-(4-(oxiran-2-yl-methoxy)phenyl)(phenyl)methanone from example 2

An oblate of pristine poly-co-ethyleneoxid-(4-(oxiran-2 ylmethoxy)phenyl)(phenyl) methanone (2) was placed between the two plates in a rheometer (parallel plate configuration, bottom plate is a quartz glass plate). The distance between the plates was set to 0.3 mm and the temperature to 120° C. The measurements were run with a fixed strain of 1% and a constant frequency of 1 Hz. When the loss and storage modules had stabilized, a UV-lamp was turned on, thus irradiating the sample through the bottom plate on the rheometer via a fibre from the lamp. The loss and storage modules were then followed as a function of time, while the UV-lamp irradiated the sample. An illustrative result of such a measurement is shown in FIG. 5.

Figure 5:
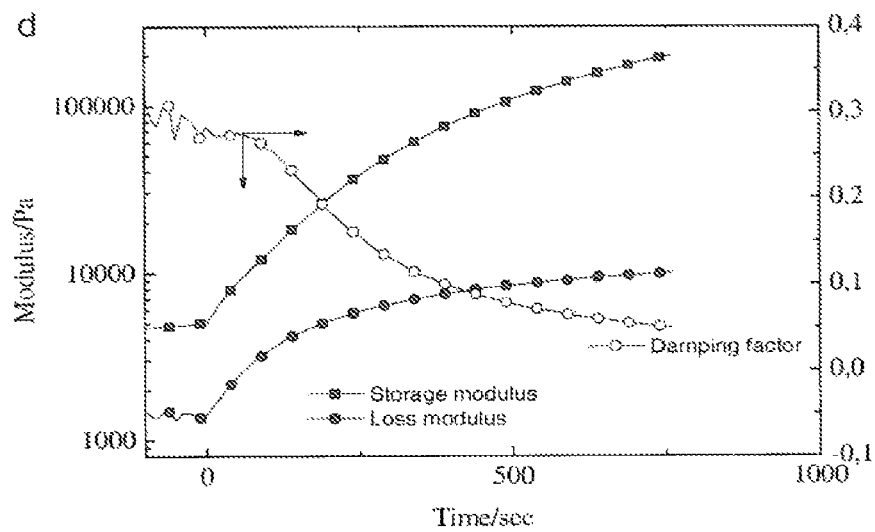
FIG. 5 shows the curing profile for pristine poly-co-ethyleneoxid-(4-(oxiran-2-ylmethoxy)phenyl)(phenyl)methanone (2) at 120° C.
Figure 6:
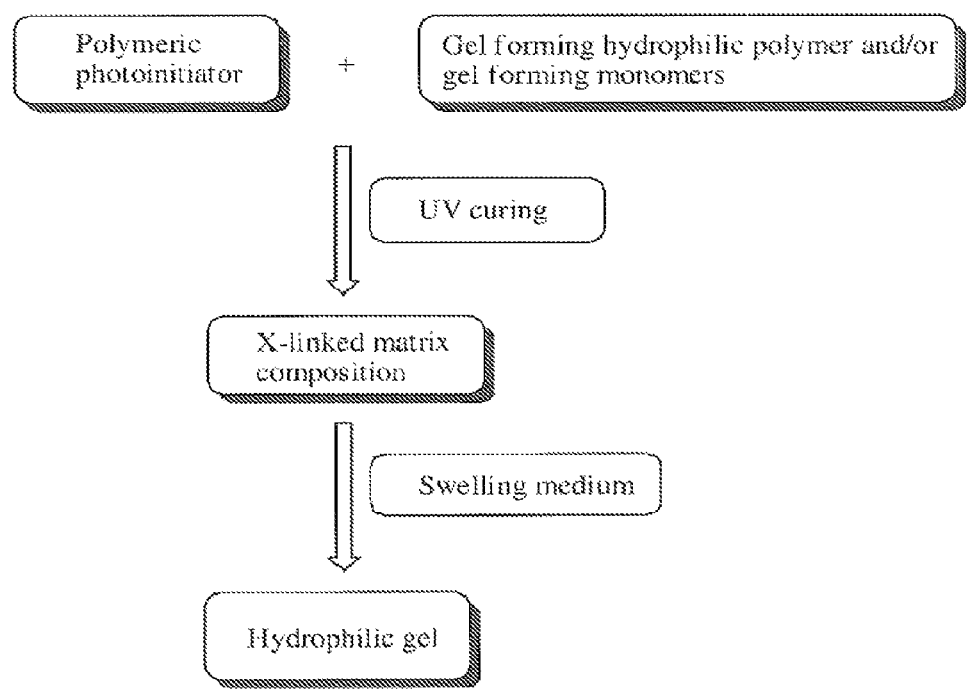
FIG. 6 is a schematic illustration of the method(s) of the invention.

As seen from FIG. 5, the polymer indeed responds to UV irradiation, however, the initial values of the modulus indicates a solid (damping factor is lower than one). Upon exposure to UV irradiation the sample shows an increase in both storage and loss modulus indicating that cross-linking is taking place.

When the UV source is turned on, both modulus (G' and G") increases in value which indicates that cross-linking is indeed taking place.

What is claimed:
1. A method for manufacturing a catheter comprising a hydrophilic gel, said method comprising the steps of:
a) combining a polymeric photoinitiator of the general formula I:

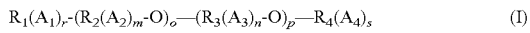

wherein $R_2$ and $R_3$ are independently at each occurrence identical or different, linear or branched alkylene or cycloalkylene groups; wherein $R_2$ and $R_3$ may be substituted with one or more substituents selected from CN; azides, esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;
$R_1$ and $R_4$ are independently at each occurrence identical or different, linear or branched alkyl or cycloalkyl groups or aryl groups or are independently at each occurrence selected from H, OH, CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, polyethylenes, polyethylene oxides, polyvinyl pyrrolidones, polypropylenes, polyesters, polyamides, polyacrylates, polystyrenes, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;

o and p are each a real number from 0-5000 provided that o+p>0;

m and n are each a real number from 0-10, provided that m+n>0;

r and s are each a real number from 0-5;

provided at least one of m or n is at least 1; and $A_1$, $A_2$, $A_3$ and $A_4$ are identical or different photoinitiator moieties linked to $R_1$, $R_2$, $R_3$, and $R_4$, respectively, via an alkylene ether spacer group comprising (—$CH_2CH_2$—O)$_t$—, wherein t is from 1-100;

with one or more gel-forming polymers and/or gel-forming monomers to form a matrix composition, b) curing the matrix composition obtained in step a. by exposing it to UV radiation, c) exposing the matrix composition to a swelling medium, d) incorporating the hydrophilic gel/matrix composition into a catheter, wherein steps b) and c) may take place in any order, provided that, if step d) is carried out first, step b) takes place before step c).

2. The method according to claim 1, wherein $R_2$=—$CH_2CH_2$—, in which one or more H atoms may be replaced by $A_2$.

3. The method according to claim 1, wherein $R_3$=—$CH_2CH_2$—, in which one or more H atoms may be replaced by $A_3$.

4. The method according to claim 1, wherein $R_1$ and $R_4$=—$CH_2CH_2$—, in which one or more H atoms may be replaced by $A_1$ or $A_4$, respectively.

5. The method according to claim 1, wherein $R_1$=OH.

6. The method according to claim 1, wherein $R_4$=H.

7. The method according to claim 1, wherein $A_1$, $A_2$, $A_3$ and $A_4$ are identical or different photoinitiator moieties selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, silane, maleimides, and derivatives thereof.

8. The method according to claim 1, wherein $A_1$, $A_2$, $A_3$ and $A_4$ are identical or different photoinitiator moieties selected from the group consisting of 2-hydroxy-2-methyl-propiophenone, benzophenone, thioxanthone, benzil, anthraquionone, camphorquinone, benzoin ether, acylphosphine oxide, silane, and derivatives thereof.

9. The method according to claim 1, wherein $A_1$, $A_2$, $A_3$ and $A_4$ are identical photoinitiator moieties.

10. The method according to claim 1, wherein $A_1$, $A_2$, $A_3$ and $A_4$ are at least two different photoinitiator moieties.

11. The method according to claim 1, wherein at least one of $A_1$, $A_2$, $A_3$ and $A_4$ is a benzophenone photoinitiator moiety.

12. The method according to claim 1, wherein at least $A_2$ and $A_3$ are benzophenone photoinitiator moieties.

13. The method according to claim 1, wherein o and p are each from 0-3000, provided that o+p>0.

14. The method according to claim 1, wherein m and n are each an integer of from 0-8, provided that m+n>0.

15. The method according to claim 1, wherein m=1, n=0 and the ratio o:p is at least 1:1000.

16. The method according to claim 1, wherein r and s are each from 0-4.

17. The method according to claim 1, wherein the polymeric photoinitiator has a molecular weight between 5 kDa and 10,000 kDa.

18. The method according to claim 1, wherein $R_1$ and $R_4$ are selected from the group consisting of polyacrylates, polyethylene oxides, polyvinyl pyrrolidones, polyesters, polyamides, and polyurethanes.

19. The method according to claim 1, wherein $R_1$ and $R_4$ are each independently selected from $C_1$-$C_{25}$ linear alkyl, $C_3$-$C_{25}$ branched alkyl, and $C_3$-$C_{25}$ cycloalkyl.

20. The method according to claim 1, wherein the gel-forming polymer is selected from the group consisting of polyacrylates, polyalkylethers, polyurethanes, polyethylene vinyl acetates, polyvinylpyrrolidone, and co-polymers and blends thereof.

21. The method according to claim 1, wherein the gel-forming monomer is selected from the group consisting of acrylate monomers, N-vinylpyrrolidone, and epoxide monomers.

22. The method according to claim 1, wherein step b) takes place before step c).

* * * * *